(12) United States Patent
Baird et al.

(10) Patent No.: US 7,602,193 B1
(45) Date of Patent: Oct. 13, 2009

(54) RF WAVEGUIDE MODE SUPPRESSION IN CAVITIES USED FOR MEASUREMENT OF DIELECTRIC PROPERTIES

(75) Inventors: J. Mark Baird, Sandy, UT (US); Darren J. Corey, Salt Lake City, UT (US)

(73) Assignee: L-3 Communications Corporation, New York, NY (US)

( * ) Notice: Subject to any disclaimer, the term of this patent is extended or adjusted under 35 U.S.C. 154(b) by 223 days.

(21) Appl. No.: 11/801,956

(22) Filed: May 11, 2007

(51) Int. Cl.
*G01R 27/04* (2006.01)
*G01R 27/28* (2006.01)

(52) U.S. Cl. .................. 324/633; 324/636; 324/655
(58) Field of Classification Search ............ 324/633, 324/655, 636
See application file for complete search history.

(56) References Cited

U.S. PATENT DOCUMENTS

| | | | | |
|---|---|---|---|---|
| 2,756,389 A | * | 7/1956 | Stinehelfer | 324/76.51 |
| 3,250,985 A | * | 5/1966 | Hyde | 324/316 |
| 4,429,656 A | * | 2/1984 | Weisenberger | 116/137 R |

OTHER PUBLICATIONS

Janezic, M. D. et al., "Relative Permittivity and Loss Tangent Measurement using NIST 60 mm Cylindrical Cavity," Aug. 2005, 66 pp., National Institute of Standards and Technology (NIST) Special Publication 260-159.*

Baker-Jarvis, J. et al., "Dielectric Characterization of Low-Loss Materials A Comparison of Techniques," Aug. 4, 1998, pp. 571-577, IEEE Transactions on Dielectrics and Electrical Insualtion, vol. 5, No. 4.*

Jeffries, D., "Waveguides and Cavity Resonators," Jan. 14, 2005, 10 pp.

Vankatesh, M.S. et al., "An overview of dielectric properties measuring techniques," 2005, 4 pp., Canadian Biosystems Engineering, vol. 47.

Coakley, K. J. et al., "Estimation of Q-Factors and Resonant Frequencies," Mar. 2003, pp. 862-868, IEEE Transactions on Microwave Theory and Techniques, vol. 51, No. 3.

Janezic, M. D. et al., "Relative Permittivity and Loss Tangent Measurement using NIST 60 mm Cylindrical Cavity," Aug. 2005, 66 pp., National Institute of Standards and Technology (NIST) Special Publication 260-159.

Baker-Jarvis, J. et al., "Dielectric Characterization of Low-Loss Materials A Comparison of Techniques," Aug. 4, 1998, pp. 571-577, IEEE Transactions on Dielectrics and Electrical Insulation, vol. 5, No. 4.

* cited by examiner

*Primary Examiner*—Timothy Dole
*Assistant Examiner*—Farhana Hoque
(74) *Attorney, Agent, or Firm*—Harrington & Smith, PC

(57) ABSTRACT

The exemplary embodiments of the invention provide techniques that assist in the absorption, reduction or elimination of the resonance of unwanted cavity modes in a cavity measurement system, such as a cylindrical $TE_{0,n}$ cavity measurement system used to measure various dielectric properties of a dielectric sample, for example. One non-limiting, exemplary system includes: sidewalls; a first endplate; a second endplate disposed opposite the first endplate so as to define a cavity bounded by the sidewalls, the first endplate and the second endplate; and first and second radio frequency (RF) coupling receptacles coupled to at least one of the sidewalls, the first endplate or the second endplate, wherein the first and second RF coupling receptacles are configured to pass a RF signal through the cavity. The first endplate has a plurality of conducting loops disposed on a surface facing the second endplate. Each loop of the plurality of conducting loops is electrically isolated from other loops of the plurality of conducting loops.

24 Claims, 5 Drawing Sheets

FIG. 1 – PRIOR ART

RF WAVEGUIDE MODE SUPPRESSION IN CAVITIES USED FOR MEASUREMENT OF DIELECTRIC PROPERTIES

TECHNICAL FIELD

These teachings relate generally to a cavity measurement system for measuring electrical properties of materials and, more specifically, relate to suppressing unwanted radio frequency modes in a cavity used for measuring dielectric constants and loss tangents in dielectric materials.

BACKGROUND

Materials engineering continues to develop new plastics and ceramics, many of which may be appropriate for use in radio frequency (RF) devices. Low loss dielectric materials are measured to ascertain their qualities and potential applications. A number of techniques and apparatus exist to assist in the measurements. One such system utilizes the cavity resonance technique to measure the dielectric constants and loss tangents of materials. The materials measured may include plastic and ceramic materials used in RF devices. For example, antennas may require that low loss dielectric materials be used in the construction of antenna feed and radome systems.

The cavity resonance technique employs a resonant cavity in which the sample to be measured is placed. The resonant cavity is designed in the standard TE (transverse electric) or TM (transverse magnetic) mode of propagation of the electromagnetic fields, for example. The technique is based on an accurate model of the resonant frequency and volumetric absorption characteristics of the cavity. The sample completely fills a slice through the waveguide cross section (e.g., rectangular or cylindrical) so that it can be accurately modeled as a short length of filled waveguide transmission line. With such an accurate model, the values of the dielectric constant and loss tangent can then be varied within the model to provide correspondence with the cavity measurements. The final values required to produce a match are the measured values. Changes in the center frequency and width of the resonance transmission based on the insertion of the sample provide information that may be used to calculate the dielectric constant. Changes in the Q-factor (ratio of energy stored to energy dissipated) are used to estimate the dielectric loss. See Vankatesh, M. S. and Raghavan, G. S. V. 2005. "An overview of dielectric properties measuring techniques." Canadian Biosystems Engineering/Le génie des biosystèmes au Canada 47:7.15-7.30, 7.18-7.19.

For general information concerning waveguides and cavity resonators, see generally D. Jeffries, "Waveguides and Cavity Resonators," Jan. 14, 2005. The precise calculations employed in analyzing the measurements and estimating the dielectric constant and loss tangents of materials, for example, are known to one of ordinary skill in the art. For an example of estimating the quality factor (Q) and resonant frequency ($f_0$) of a microwave cavity based on observations of a resonance curve on an equally spaced frequency grid, see Coakley et al., "Estimation of Q-Factors and Resonant Frequencies," IEEE Trans. of Microwave Theory and Techniques, Vol. 51, No. 3, pp. 862-868, March 2003.

An example conventional $TE_{0,n}$ waveguide cavity measurement system 10 is shown in FIG. 1. The system 10 generally includes a metal cylinder (that is, sidewalls) 12 with a moveable endplate 14 on the bottom (for fine tuning of a cylindrical cavity 22 and insertion of a dielectric sample 16), a fixed endplate 18 on the top and coupling apertures (that is, coupling holes or coupling receptacles) 20, also on the top and passing through the fixed endplate 18. The coupling holes 20 permit a signal to pass through the cavity 22 where the dielectric sample 16 sits. The dielectric sample 16 is in the shape of a cylindrical disc. For this example, assume the cavity 22 is designed to resonate in the low-loss $TE_{0,n}$ modes. In the conventional system 10 of FIG. 1, additional components are also shown, including: a surrounding layer of water 24 and temperature sensing probe 26 for thermally isolating the cavity 22 and measuring the temperature of the water 24 (the water jacket 24 may be connected to a water bath that controls its temperature); a detachable tuner assembly 28, tuner position sensing micrometer 30 and motor-driven micrometer 32 for finely-tuned moving of the moveable endplate 14; and a helical waveguide 34 that lines the interior wall of the cavity 22 (as further explained below). See J. Baker-Jarvis, R. G. Geyer, J. H. Grosvenor, Jr., et al., "Dielectric Characterization of Low-loss Materials—A Comparison of Techniques", IEEE Trans. on Dielectrics and Electrical Insulation, Vol. 5 No. 4, pp. 571-577, August 1998.

Specific cavity modes can be observed. However, generally the cavity is overmoded and other, undesirable cavity modes are free to resonate unless otherwise suppressed. The unwanted cavity modes can interfere with the otherwise accurate measuring process.

One conventional method for suppressing the unwanted modes is to use fine conducting wire to form a helically-wound wall over the interior length of the cylindrical cavity. See, e.g. Baker-Jarvis et al.; Janezic et al., "Relative Permittivity and Loss Tangent Measurement using NIST 60 mm Cylindrical Cavity," National Institute of Standards and Technology (NIST) Special Publication 260-159, August 2005, p. 4. The helical waveguide 34 (see FIG. 1) allows only azimuthal wall currents and permits only the desired $TE_{0,n}$ waveguide modes to propagate, thereby attenuating unwanted modes.

SUMMARY

In an exemplary aspect of the invention, a measurement system is provided. The system includes: sidewalls; a first endplate; a second endplate disposed opposite the first endplate so as to define a cavity bounded by the sidewalls, the first endplate and the second endplate; and first and second radio frequency (RF) coupling receptacles coupled to at least one of the sidewalls, the first endplate or the second endplate, wherein the first and second RF coupling receptacles are configured to pass a RF signal through the cavity. The first endplate has a plurality of conducting loops disposed on a surface facing the second endplate. Each loop of the plurality of conducting loops is electrically isolated from other loops of the plurality of conducting loops. The second endplate has first and second regions. The first region is made of a material that is substantially non-lossy at frequencies of interest, and the second region includes a lossy material.

In another exemplary aspect of the invention, a measurement system is provided. The system includes: sidewalls; a first endplate; a second endplate disposed opposite the first endplate so as to define a cavity bounded by the sidewalls, the first endplate and the second endplate; and first and second radio frequency (RF) coupling receptacles coupled to at least one of the sidewalls, the first endplate or the second endplate, wherein the first and second RF coupling receptacles are configured to pass a RF signal through the cavity. The first endplate has a plurality of conducting loops disposed on a surface facing the second endplate. Each loop of the plurality of conducting loops is electrically isolated from other loops of the plurality of conducting loops.

In a further exemplary aspect of the invention, a measurement system is provided. The system includes: sidewalls; a first endplate; a second endplate disposed opposite the first endplate so as to define a cavity bounded by the sidewalls, the first endplate and the second endplate; and first and second radio frequency (RF) coupling receptacles coupled to at least one of the sidewalls, the first endplate or the second endplate, wherein the first and second RF coupling receptacles are configured to pass a RF signal through the cavity. The second endplate has first and second regions. The first region is made of a material that is substantially non-lossy at frequencies of interest, and the second region includes a lossy material.

In another exemplary aspect of the invention, a measurement system is provided. The system includes: sidewalls; an endplate, wherein the endplate and the sidewalls define a cavity bounded by the endplate and the sidewalls; and first and second radio frequency (RF) coupling receptacles coupled to at least one of the sidewalls or the endplate, wherein the first and second RF coupling receptacles are configured to pass a RF signal through the cavity. The endplate has a suppression unit operable to suppress undesired resonant modes.

BRIEF DESCRIPTION OF THE DRAWINGS

The foregoing and other aspects of embodiments of this invention are made more evident in the following Detailed Description, when read in conjunction with the attached Drawing Figures, wherein.

DETAILED DESCRIPTION

As noted above, it would be desirable to provide additional techniques that assist in the absorption, reduction or elimination of the resonance of unwanted cavity modes in a cavity measurement system.

Figure 2:
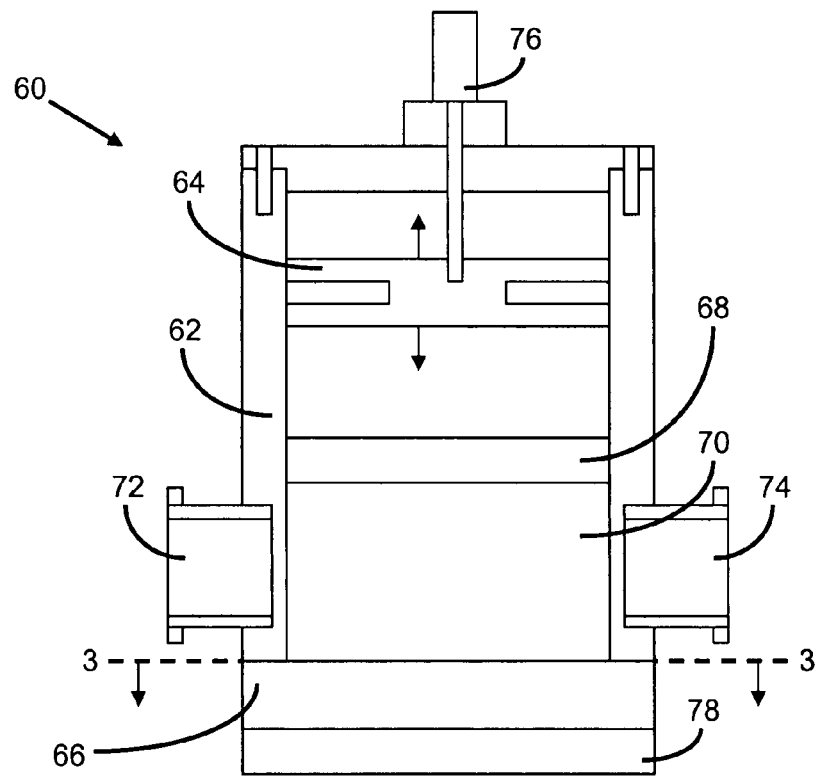
FIG. 2 shows an exemplary cavity measurement system incorporating aspects of the invention.

FIG. 2 shows an exemplary cavity measurement system 60 incorporating aspects of the invention. The system 60 generally includes a metal cylinder (that is, sidewalls) 62 with a moveable endplate 64 disposed towards the top and a fixed endplate 66 on the bottom. A dielectric sample 68 can be placed within a cavity 70 defined by the system 60, between the moveable endplate 64 and the fixed endplate 66. The dielectric sample 68 is preferably in the shape of a cylindrical disc and preferably extends across the entire breadth of the cavity (that is, substantially touching an entire interior circumference of the cylinder 62). The cylinder 62, the fixed endplate 66 and one of the sample 68 or the moveable endplate 64 (depending on if the sample 68 is situated within the system 60 or not, respectively) define the cavity 70. Two coupling apertures 72, 74 permit a RF signal to pass through the cavity 70.

Figure 1:
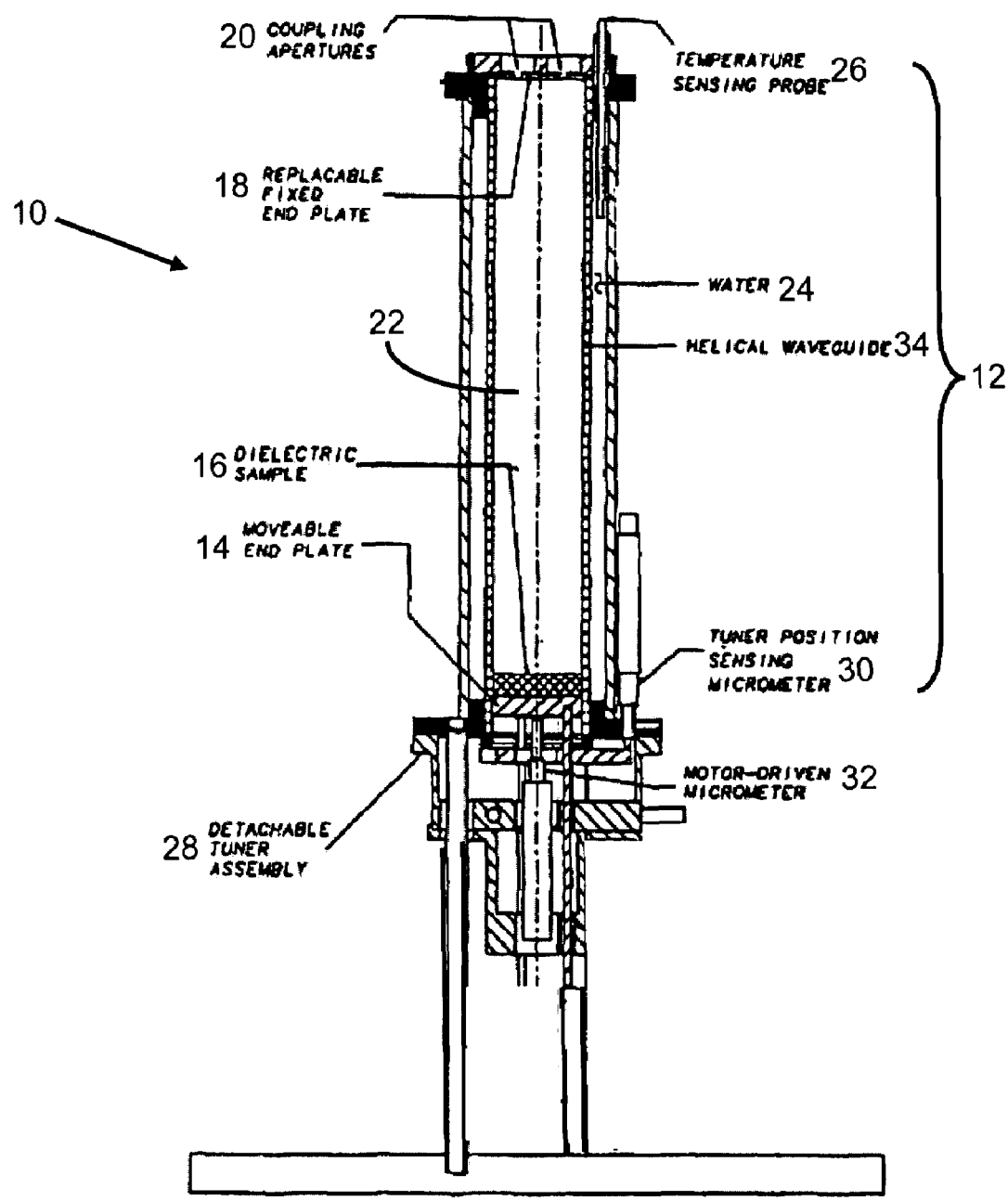
FIG. 1 shows an example conventional $TE_{0,n}$ waveguide cavity measurement system.

Although shown using a cylindrical cavity measurement system, the invention may also be used with other, non-cylindrical cavity measurement systems. Furthermore, the specific design of the system may vary in various ways. As a non-limiting example, the moveable endplate 64 may be located at the top of the system as in FIG. 2, or the relative positions of the endplates 64, 66 may be reversed. As an additional non-limiting example, and also as shown in FIG. 2, the coupling holes may be located towards the bottom of the system instead of at the top (see FIG. 1). As a further non-limiting example, although, as noted below, it is assumed that the cavity 70 is designed to resonate in the low-loss $TE_{0,n}$ modes, the cavity may be designed or arranged for different TE modes or TM modes. Furthermore, although described herein as being made of metal, those of skill in the art will appreciate that the cylinder (that is, the sidewalls) may be made using any material that is substantially non-lossy at frequencies of interest (that is, any suitable material). Typically a suitable metal is used for the cylinder. In addition, the cylinder may be a monolithic piece of one material, a piece made from a combination of materials or a layer of suitable material disposed on another piece or material, as non-limiting examples. Furthermore, although illustrated with respect to a closed system, the exemplary embodiments of the invention may be employed with an open or unbounded system, such as a high-Q Fabre-Perot system, as a non-limiting example. In other embodiments, the system may comprise an overmoded waveguide cavity that uses, for example, the $TE_{1,0}$ mode. Such an overmoded system may itself comprise a pattern of vertical conducting wires to produce good reflection and suppress unwanted modes. In addition, although the system is described with respect to a dielectric sample, in other embodiments the system, or one similar to it, may be employed for measuring other types of samples or for other purposes for which the system may be suitable.

The measurement process is as follows. First, the empty cavity is measured to calibrate the wall-loss and coupling constants in a mathematical model of the system. Then, a sample of the dielectric material to be measured is introduced into the cavity. The relative dielectric constant ($\in_r$) and the loss tangent (tan δ) in the model are automatically changed (optimized) until the model transmission coefficient ($S_{2,1}$) matches the network analyzer measurement of the loaded cavity. The result is a very sensitive measurement of both $\in_r$ and tan δ with sensitivities typically in the third or fourth significant figure, for example.

The measurement process proceeds as explained above, with a rotating mechanism 76 (e.g., a servo) enabling finely-tuned movement of the moveable endplate 64. As with the conventional system of FIG. 1, assume that the cavity 70 is designed to resonate in the low-loss $TE_{0,n}$ modes. The design of the fixed endplate 66 and the design of the moveable endplate 64 are further explained below and with reference to FIGS. 3-8. Note that the system 60 also includes lossy material 78 (such as an RF absorber, for example) located underneath the fixed endplate 66. Non-limiting examples of the lossy material 78 include ferrite tiles, polyurethane foam, polystyrene foam and hybrid absorber material. The purpose of the lossy material 78 is explained below with respect to FIG. 3, in conjunction with a detailed explanation of the fixed endplate 66.

Figure 3:
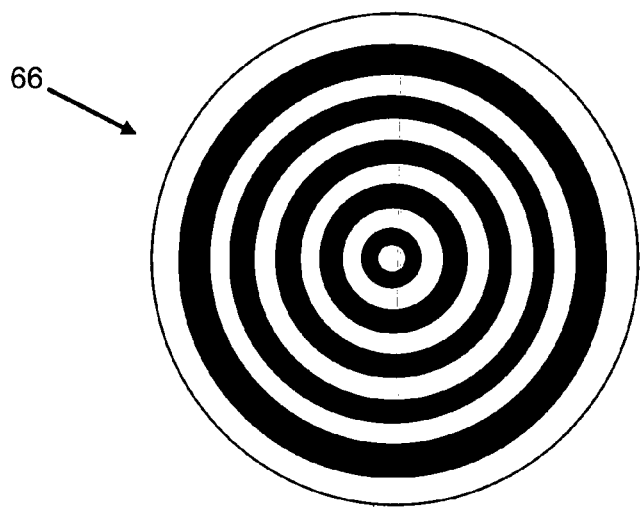
FIG. 3 shows a sectional view taken across section line 3 in FIG. 2, illustrating an exemplary design for the fixed endplate of FIG. 2.

FIG. 3 shows a sectional view taken across section line 3 in FIG. 2, illustrating an exemplary design for the fixed endplate 66 of FIG. 2. As apparent in FIG. 3, the fixed endplate 66 comprises a finely-spaced set of concentric rings or loops of conducting material on a circuit board. As utilized herein, loop refers to a closed pathway. As shown in FIG. 3, there is equi-distant spacing of one loop to its neighboring loop(s) about the circumference. The loops do not intersect one another as they are a series of concentric circles. No conductive material is located at the center of the loops. Each loop has a substantially constant width about its circumference and each loop defines substantially the same width. The concentric circular rings may be considered as, for example, a "metal screen mode filter." In other embodiments, the rings are formed in the top metallization of the circuit board. The rings are preferably relatively thin in thickness. In other embodiments, it may be advantageous to have the thickness of the rings comprise a value that is two to three times the spacing (e.g., the separation) between the rings. If the thickness of the rings is too thin, there may be some leakage of the $TE_{0,n}$ modes due to evanescent mode leakage through the screen.

The circuit board preferably has a thin dielectric with the bottom conductor removed. The cylindrical cavity measurement system 60 with the fixed endplate 66 removed is placed on top of the circuit board such that the concentric rings provide the bottom wall of the cavity 70. By utilizing this design for the fixed endplate 66, all of the cavity modes except, for example, the $TE_{0,n}$ modes leak energy through the fixed endplate 66 allowing the lossy material 78 placed under the circuit board to absorb these fields. This design for the fixed endplate 66 only supports the azimuthal currents on the bottom wall of the cavity 70. Of the designs herein presented for a fixed endplate in a cavity measurement system, the design shown in FIG. 3 is seen as most advantageous.

Figure 4:
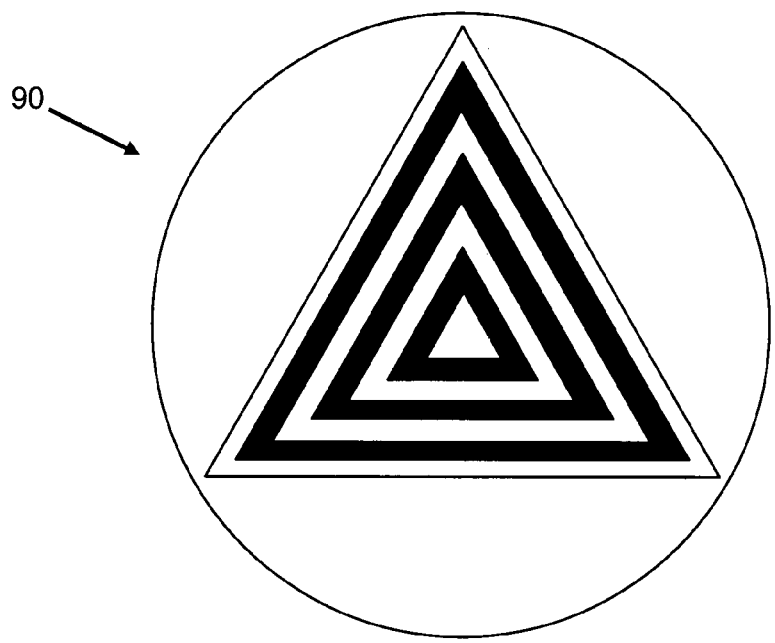
FIG. 4 is similar to FIG. 3, depicting another exemplary embodiment for the fixed endplate of the cavity measurement system incorporating aspects of the invention.

FIG. 4 is similar to FIG. 3, depicting another exemplary embodiment 90 for a fixed endplate of the cavity measurement system incorporating aspects of the invention. The fixed endplate 90 of FIG. 4 comprises a finely-spaced set of concentric triangles of conducting material on a substrate.

Figure 5:
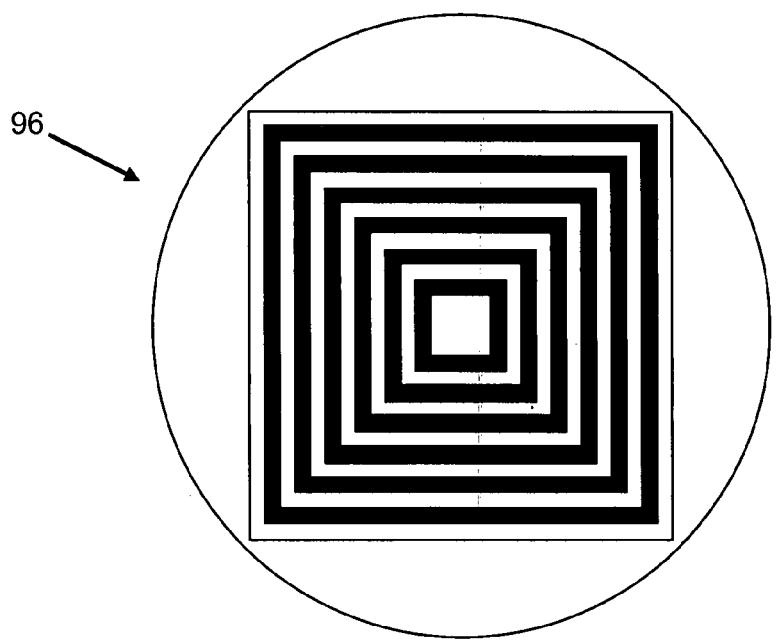
FIG. 5 is similar to FIG. 3, showing another exemplary embodiment for the fixed endplate of the cavity measurement system incorporating aspects of the invention.

FIG. 5 is similar to FIG. 3, showing another exemplary embodiment 96 for a fixed endplate of the cavity measurement system incorporating aspects of the invention. The fixed endplate 96 of FIG. 5 comprises a finely-spaced set of concentric squares of conducting material on a substrate.

As is apparent from FIGS. 3-5, any suitable, finely-spaced set of shapes may be employed. Preferably, the modes of the system and further experimentation with individual systems and setups will dictate the specific parameters (such as the spacing, size, shape and conducting material of the finely-spaced set of shapes, as non-limiting examples) of the fixed endplate.

Although shown in FIGS. 3-5 as a finely-spaced set of substantially similar, concentric shapes, in other embodiments the shapes may not be concentric. In further embodiments, the shapes may not be substantially similar. In further embodiments, shapes other than those shown in FIGS. 3-5 may be utilized.

The circuit board can be constructed using microstrip technology, as a non-limiting example. Although a circuit board is employed, any suitable substrate may be used. In other embodiments, the thin dielectric with the bottom conductor removed may not be present on the circuit board or substrate. Although shown in FIG. 3 with concentric circles, it will be appreciated that a circle is simply a special case of an ellipse and that in other embodiments, a series of concentric ellipses may be employed. As used herein, concentric ellipses refer to a plurality of ellipses that utilize substantially the same foci in forming the ellipses. In further embodiments, the plurality of ellipses may not be concentric with different ellipses utilizing different foci. In other embodiments, there may not be equi-distant spacing of one loop to its neighboring loop(s) about the circumference. In further embodiments, the loops may intersect one another. In other embodiments, conductive material may be located at the center of the loops. In further embodiments, each loop may not have a substantially constant width about its circumference. In other embodiments, each loop may not define substantially the same width.

Figure 6:
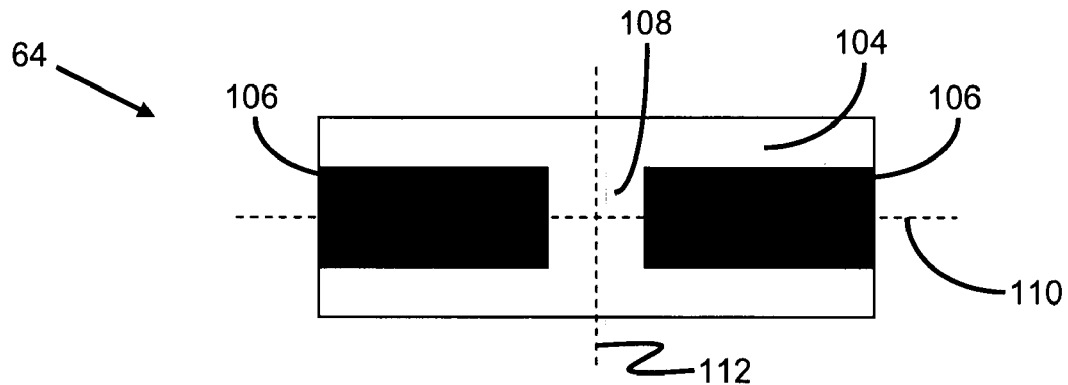
FIG. 6 is a sectional view of an exemplary design for the moveable endplate of FIG. 2.

FIG. 6 is a sectional view of an exemplary design for the moveable endplate 64 of FIG. 2. The moveable endplate 64 comprises two regions: a contact region 104 and a non-contact region 106. The view of the moveable endplate 64 shown in FIG. 6 is a sectional view. That is, the moveable endplate 64 is of a generally cylindrical shape to match the cross-section of the cylindrical cavity 70 and preferably extends across the entire breadth of the cavity 70 (that is, substantially touching an entire interior circumference of the cylinder 62). As such, the non-contact region 106 is generally in the shape of a torus with a central pillar 108 of the contact region 104 at the central axis of the torus. As is apparent, the cross-sectional shape of the torus is two rectangles. Note that the contact region 104 includes the portion of the moveable endplate 64 (that is, the surface of the moveable endplate 64) that, in the absence of a sample 68, faces the cavity 70, forming one of the boundary walls that define in part the cavity 70.

As referred to herein, a torus, a toroid or a toroidal shape is considered to be a three dimensional surface generated by a closed curve rotating about, but not intersecting or containing, an axis in its own plane. One non-limiting example of a torus is a doughnut. The sectional or cross-sectional shape of a torus refers to the closed curve (that is, the two-dimensional shape) that is rotated in order to form the torus. By definition, due to the rotational element, a torus or toroidal shape necessitates a circular shape or circular attribute. If a non-cylindrical or non-circular cavity is employed in a cavity measurement system, the non-contact region of the moveable endplate will not generally be in a toroidal shape.

Preferably the contact region 104 is made of a material that is substantially non-lossy at frequencies of interest (that is, any suitable material), forming the body of the moveable endplate 64. The contact region 104 is typically made of metal, such as brass, though the exemplary embodiments of the invention are not limited thereto. In addition, the contact region 104 may be a monolithic piece of one material, a piece made from a combination of materials or a layer of suitable material disposed on another piece or material, as non-limiting examples.

Preferably the non-contact region 106 is an otherwise open space filled with a lossy material (such as an RF absorber, for example). By having the non-contact region 106 include lossy material, this design assists in the absorption of unwanted modes in the cavity measurement system 60.

In other embodiments, the sectional shape of the moveable endplate may not be symmetric about either the horizontal axis 110 or the vertical axis 112. In further embodiments, the cross-sectional shape of the torus forming the non-contact region may be a shape other than a rectangle, such as a triangle, ellipse or polygon, as non-limiting examples. In other embodiments, one or more non-contact regions may include a portion of one or more (both, for example) ends of the moveable endplate (see FIGS. 7 and 8). In further embodiments, the sectional shape of the moveable endplate may not define a central pillar 108 or may include more than one such pillar. In other embodiments, the moveable endplate may have more than two regions made from two or more disparate materials. In other embodiments, such as those wherein the system does not have a generally cylindrical shape, the moveable endplate may comprise a shape other than a generally cylindrical shape. As noted above, the cross-section of the moveable endplate preferably matches the cross-section of the cavity and preferably extends across the entire breadth of the cavity. However, in further embodiments, the moveable endplate and/or fixed endplate may not extend across the entire breadth of the cavity.

In the design shown in FIG. 6, the relatively abrupt transition from the contact region 104 to the non-contact region 106, and specifically the transition to the lossy material that preferably fills the non-contact region 106, may cause RF reflection of fields that enter the non-contact region 106. Such RF reflection can impair the desired absorption and unwanted-mode attenuation properties of this design for the moveable endplate 64.

Figure 7:
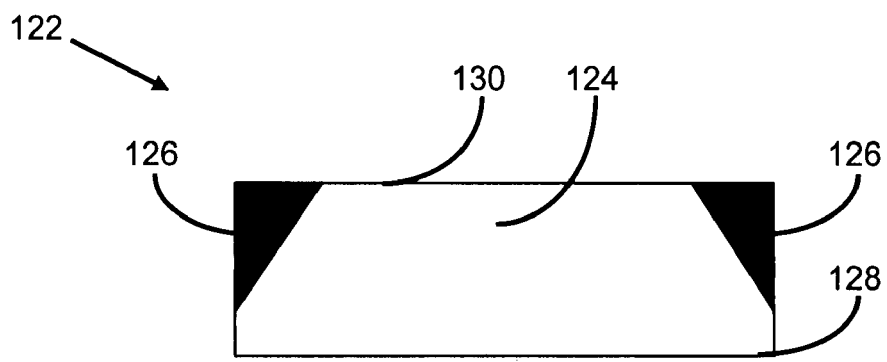
FIG. 7 shows a sectional view of another exemplary design for a moveable endplate in a cavity measurement system.

FIG. 7 shows a sectional view of another exemplary design for a moveable endplate in a cavity measurement system. As in the moveable endplate 64 of FIG. 6, the moveable endplate 122 of FIG. 7 includes two regions: a contact region 124 and a non-contact region 126. Also as in the moveable endplate 64 of FIG. 6, the moveable endplate 122 of FIG. 7 is in a generally cylindrical shape to match the cross-section of a cylindrical cavity, with the non-contact region 126 being generally in the shape of a torus with a central pillar of the contact region 124 at the central axis of the torus. As is apparent, the cross-sectional shape of the torus is a triangle in the exemplary design of FIG. 7. Preferably, the non-contact region 126 is made of a lossy material. In other embodiments, the non-contact region 126 is not entirely filled by lossy material but rather includes it as one component of the non-contact region 126.

The orientation of the moveable endplate 122 of FIG. 7 matches the orientation of the cavity measurement system 60 shown in FIG. 2. That is, a first surface (or first end) 128 of the moveable endplate 122 is that surface which, in the absence of a sample, defines in part the cavity, and forms one of the boundary walls of the cavity. The first surface 128 may also be referred to as the face that generally faces the cavity or generally faces toward the cavity. A second surface (or second end) 130 of the moveable endplate 122 is opposite the first surface 128 and generally faces away from the cavity and fixed endplate. For the exemplary embodiment shown in FIG. 7, the first surface 128 extends across the cavity (that is, substantially touching an entire interior circumference of the cylinder in this example) while the second surface 130 does not extend across the entire breadth of the cavity. Furthermore, the first surface 128 generally has a greater area than the second surface 130. As noted above, of the designs herein presented for a moveable endplate in a cavity measurement system, the design shown in FIG. 7 is seen as particularly advantageous.

The exemplary design for a moveable endplate shown in FIG. 7 addresses the potential problems with the design shown in FIG. 6 since the shape of the contact region 124 is tapered away from the first surface 128 such that the transition to greater thicknesses of the lossy material that preferably fills the non-contact region 126 is more gradual. Using the design of FIG. 7, there is minimal, if any, RF reflection of fields entering the non-contact region 126, thus reinforcing the desired properties of absorption and unwanted-mode attenuation.

Figure 8:
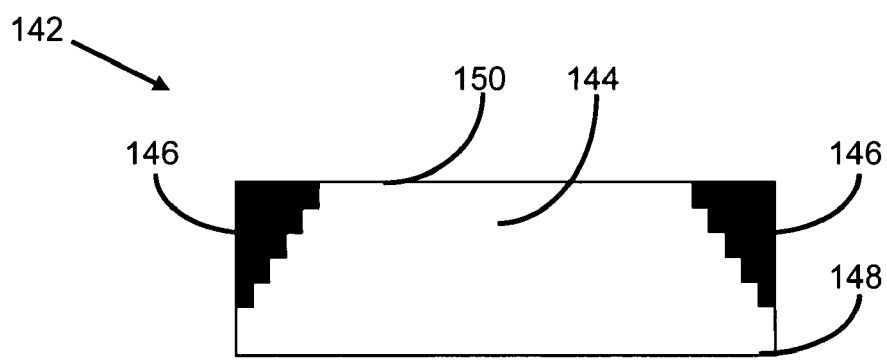
FIG. 8 illustrates a sectional view of another exemplary design for a moveable endplate in a cavity measurement system.

FIG. 8 illustrates a sectional view of another exemplary design for a moveable endplate in a cavity measurement system. The design of the moveable endplate 142 shown in FIG. 8 is similar to the design shown in FIG. 7. The moveable endplate 142 has a contact region 144 and a non-contact region 146, wherein the non-contact region 146 is generally in the shape of a torus with a central pillar of the contact region 144 at the central axis of the torus. The cross-sectional shape of the torus is a polygon having a shape similar to steps and the non-contact region preferably includes a lossy material.

The moveable endplate 142 shares a similar orientation with the moveable endplate 122 of FIG. 7, with a first surface 148 facing towards the cavity and a second surface 150 opposite the first surface, facing away from the cavity. The first surface 148 extends across the cavity and the first surface 148 generally has a greater area than the second surface 150. The transition to greater thicknesses of the lossy material that preferably fills the non-contact region 146 is relatively gradual due to the stepped shape of the contact region 144. As such, there is minimal, if any, RF reflection of fields entering the non-contact region 146, thus reinforcing the desired properties of absorption and unwanted-mode attenuation.

Note that, as illustrated in the endplate designs of FIGS. 6-8, the surface facing towards the cavity preferably extends across the breadth of the cavity. This generally provides a uniform, flat-plane reflection of desired modes. However, in other embodiments, the surface of the moveable endplate, or fixed endplate, facing towards the cavity may not extend across the breadth of the cavity.

As a brief summary of the moveable endplate designs presented above in FIGS. 6-8, each moveable endplate design has at least two regions: a first region (also referred to as a contact region) and a second region (also referred to as a non-contact region). The contact region refers to the region that has a portion of the moveable endplate that has contact with or faces towards the cavity in the cavity measurement system. The contact region also has at least a portion thereof that extends across the entire breadth of the portion of the system wherein the moveable endplate is located (the cavity, for example). The non-contact region is preferably in the general shape of a torus with a central pillar of the contact region at the central axis of the torus. The non-contact region preferably has lossy material. Furthermore, the transition to greater thicknesses of the lossy material that preferably fills the non-contact region is gradual as opposed to abrupt.

Although presented above in FIGS. 2-5 for a fixed endplate and in FIGS. 2 and 6-9 for a moveable endplate, the designs are applicable for any endplate in a cavity measurement system. That is, the designs presented in FIGS. 3-5 may be applied to any endplate, including the moveable endplate, and the designs presented in FIGS. 6-8 may be applied to any endplate, including the fixed endplate. Furthermore, although the system 60 of FIG. 2 incorporates aspects of the invention with respect to both the design of the fixed endplate and the design of the moveable endplate, aspects of the invention may be utilized with respect to only one endplate in a cavity measurement system.

Figure 9:
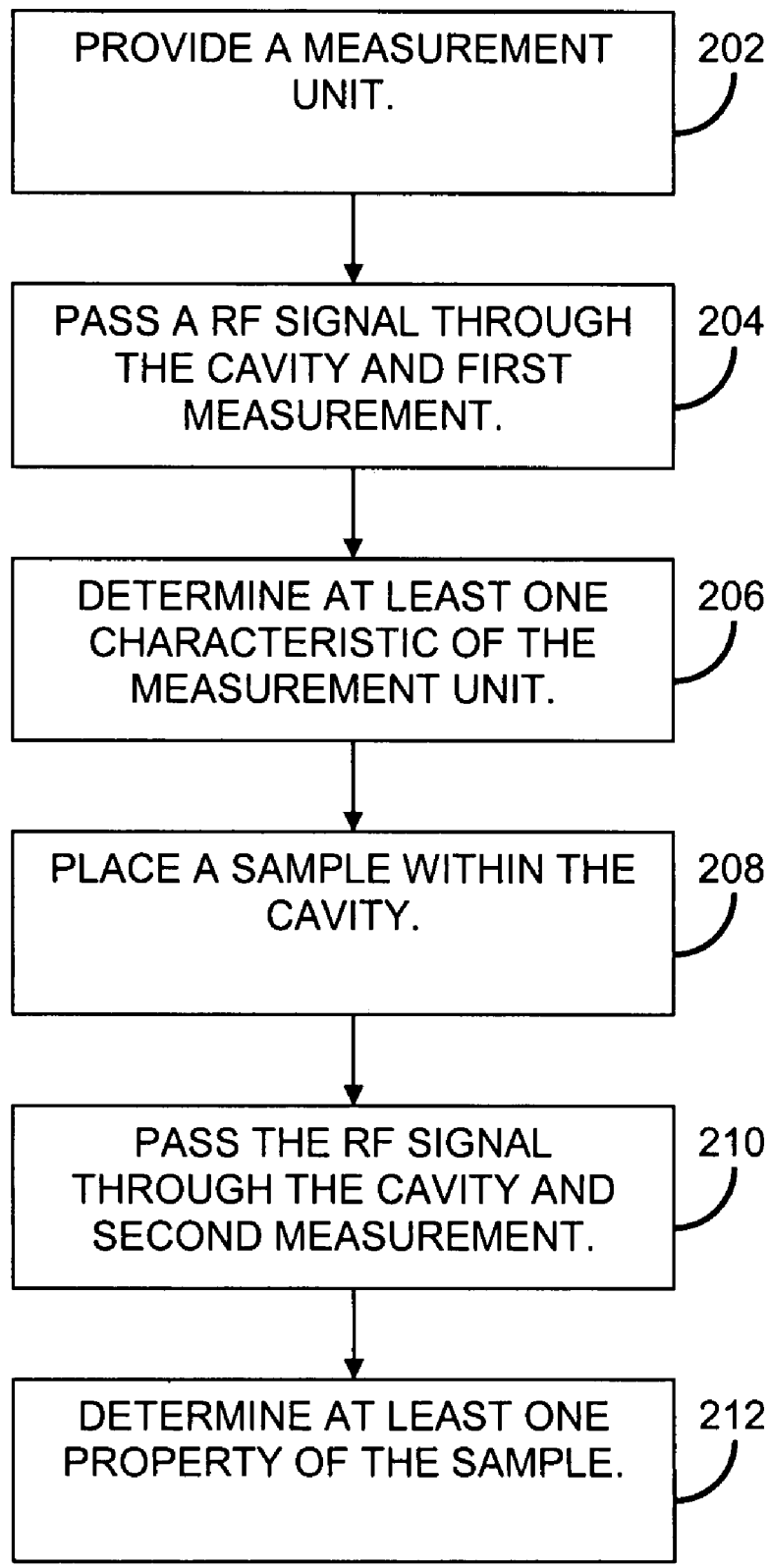
FIG. 9 depicts a flowchart illustrating one non-limiting example of a method for practicing the exemplary embodiments of this invention.

FIG. 9 depicts a flowchart illustrating one non-limiting example of a method for practicing the exemplary embodiments of this invention. In box 202, a measurement unit is provided. The measurement unit has sidewalls, a first endplate, a second endplate and first and second radio frequency (RF) coupling receptacles. The second endplate is disposed opposite the first endplate so as to define a cavity bounded by the sidewalls, the first endplate and the second endplate. The RF coupling receptacles are coupled to at least one of the sidewalls, the first endplate or the second endplate. At least one of the first endplate or the second endplate has a suppression unit operable to suppress undesired resonant modes. In box 204, a RF signal is passed through the cavity using the first and second RF coupling receptacles and at least one first measurement is performed. In box 206, using a result of the at least one first measurement, at least one characteristic of the measurement unit is determined. In box 208, a sample is placed within the cavity. In box 210, the RF signal is passed through the cavity using the first and second RF coupling receptacles and at least one second measurement is performed. In box 212, using a result of the at least one second measurement and a mathematical model of the measurement unit that is determined at least in part by the result of the at least one first measurement, at least one property of the sample is determined.

In other embodiments, the suppression unit includes a plurality of conducting loops disposed on a surface of the at least one of the first endplate or the second endplate, with the surface facing the other of the first endplate or the second endplate, and each loop of the plurality of conducting loops is electrically isolated from other loops of the plurality of conducting loops. In further embodiments, the suppression unit has first and second regions, wherein the first region includes a material that is substantially non-lossy at frequencies of interest, and wherein the second region includes a lossy material.

In other embodiments, the suppression unit has first and second regions; the first region includes a material that is substantially non-lossy at frequencies of interest, and wherein the second region includes a lossy material; the second endplate includes the suppression unit; the second endplate has a first surface facing the first endplate and a second surface disposed opposite the first surface; the second region has a toroidal shape having a cross-section; the first surface of the second endplate consists of a first surface of the first region; the second surface of the second endplate includes a second surface of the first region and a surface of the second region; and the cross-section of the toroidal shape has a generally triangular shape so as to define a greater cross-section further from the cavity.

In further embodiments, the measurement unit further includes a movement mechanism to mechanically move one of the first endplate or the second endplate relative to the other of the first endplate or the second endplate. In other embodiments, the method includes the step of: calibrating the measurement unit by passing a RF signal through the cavity using the first and second RF coupling receptacles, performing at least one calibration measurement and, based on a result of the at least one calibration measurement, mechanically moving one of the first endplate or the second endplate using the movement mechanism. In further embodiments, the sample includes a dielectric material. In other embodiments, the determined at least one property of the dielectric material includes a dielectric constant. In further embodiments, the determined at least one property of the dielectric material includes a loss tangent. In other embodiments, the determined at least one characteristic of the measurement unit includes a wall-loss constant. In further embodiments, the determined at least one characteristic of the measurement unit includes a coupling constant.

In other embodiments, the suppression unit is a first suppression unit; the first suppression unit includes a plurality of conducting loops disposed on a surface of the at least one of the first endplate or the second endplate; the surface faces the other of the first endplate or the second endplate; each loop of the plurality of conducting loops is electrically isolated from other loops of the plurality of conducting loops; the measurement unit further includes a second suppression unit; the other of the first endplate or the second endplate includes the second suppression unit; the second suppression unit has first and second regions; the first region includes a material that is substantially non-lossy at frequencies of interest; and the second region includes a lossy material.

The disclosed techniques provide improved suppression of unwanted modes with little or no degradation to the desired modes, thus providing a more accurate and reliable way to measure the dielectric properties of materials.

While the above-presented description generally focuses on a cylindrical $TE_{0,n}$ cavity system, aspects of the exemplary embodiments may be utilized in conjunction with other types of systems based on different modes or cross-sectional shapes. As a non-limiting example, aspects of the exemplary embodiments may be utilized in a $TE_{1,0}$ cavity system.

The foregoing description has provided by way of exemplary and non-limiting examples a full and informative description of the best method and apparatus presently contemplated by the inventors for carrying out the invention. However, various modifications and adaptations may become apparent to those skilled in the relevant arts in view of the foregoing description, when read in conjunction with the accompanying drawings and the appended claims. However, all such and similar modifications of the teachings of this invention will still fall within the scope of this invention.

Furthermore, some of the features of the preferred embodiments of this invention could be used to advantage without the corresponding use of other features. As such, the foregoing description should be considered as merely illustrative of the principles of the invention, and not in limitation thereof.

What is claimed is:

1. A measurement system comprising:
   sidewalls;
   a first endplate;
   a second endplate disposed opposite the first endplate so as to define a cavity bounded by the sidewalls, the first endplate and the second endplate; and
   first and second radio frequency (RF) coupling receptacles coupled to at least one of the sidewalls, the first endplate or the second endplate, wherein the first and second RF coupling receptacles are configured to pass a RF signal through the cavity,
   wherein the first endplate comprises a plurality of coplanar conducting loops disposed on a surface facing the second endplate, wherein each loop of the plurality of conducting loops is electrically isolated from other loops of the plurality of conducting loops,
   wherein the second endplate comprises first and second regions, wherein the first region comprises a material that is substantially non-lossy at frequencies of interest, and wherein the second region comprises a lossy material.

2. A measurement system comprising:
   sidewalls;
   a first endplate;
   a second endplate disposed opposite the first endplate so as to define a cavity bounded by the sidewalls, the first endplate and the second endplate; and
   first and second radio frequency (RF) coupling receptacles coupled to at least one of the sidewalls, the first endplate or the second endplate, wherein the first and second RF coupling receptacles are configured to pass a RF signal through the cavity,
   wherein the first endplate comprises a plurality of coplanar conducting loops disposed on a surface facing the second endplate, wherein each loop of the plurality of conducting loops is electrically isolated from other loops of the plurality of conducting loops.

3. The measurement system of claim 2, wherein each of the plurality of conducting loops comprises a similar concentric geometric shape.

4. The measurement system of claim 3, wherein the similar concentric geometric shape comprises an ellipse.

5. The measurement system of claim 2, wherein the first endplate comprises an interior surface facing the cavity and an opposed exterior surface, wherein lossy material is located along the exterior surface.

6. The measurement system of claim 2, wherein the plurality of conducting loops are disposed on a substrate and the substrate is disposed on the surface.

7. The measurement system of claim 2, further comprising a mechanism to mechanically move one of the first endplate or the second endplate relative to the other of the first endplate or the second endplate.

8. The measurement system of claim 2, wherein the second endplate comprises first and second regions, wherein the first region comprises a material that is substantially non-lossy at frequencies of interest, wherein the second region comprises a lossy material, and wherein the second region comprises a generally toroidal shape.

9. A measurement system comprising:
sidewalls comprising a pattern of conducting wires;
a first endplate;
a second endplate disposed opposite the first endplate so as to define a cavity bounded by the sidewalls, the first endplate and the second endplate; and
first and second radio frequency (RF) coupling receptacles coupled to at least one of the sidewalls, the first endplate or the second endplate, wherein the first and second RF coupling receptacles are configured to pass a RF signal through the cavity,
wherein the second endplate comprises first and second regions, wherein the first region comprises a material that is substantially non-lossy at frequencies of interest, and wherein the second region comprises a lossy material.

10. The measurement system of claim 9, wherein the second endplate comprises a first surface facing the first endplate and a second surface disposed opposite the first surface, and wherein the second region comprises a generally toroidal shape having a cross-section.

11. The measurement system of claim 10, wherein the first surface of the second endplate consists of a first surface of the first region, and wherein the second surface of the second endplate consists of a second surface of the first region.

12. The measurement system of claim 10, wherein the first surface of the second endplate consists of a first surface of the first region, and wherein the second surface of the second endplate comprises a second surface of the first region and a surface of the second region.

13. The measurement system of claim 12, wherein the cross-section of the generally toroidal shape comprises a generally stepped shape so as to define a greater cross-section at a distance further from the cavity.

14. The measurement system of claim 12, wherein the cross-section of the generally toroidal shape comprises a generally triangular shape so as to define a greater cross-section at a distance further from the cavity.

15. The measurement system of claim 9, wherein a shape of a cross-section of the endplate is generally similar in shape to a cross-section of the cavity, wherein the endplate extends across an entire breadth of the cavity.

16. The measurement system of claim 2, further comprising a mechanism to mechanically move one of the first endplate or the second endplate relative to the other of the first endplate or the second endplate.

17. The measurement system of claim 9, wherein the first endplate comprises a plurality of conducting loops disposed on a surface facing the second endplate, wherein each loop of the plurality of conducting loops is electrically isolated from other loops of the plurality of conducting loops, wherein each of the plurality of conducting loops comprises a similar concentric geometric shape.

18. A measurement system comprising:
sidewalls comprising a pattern of conducting wires;
an endplate, wherein the endplate and the sidewalls define a cavity bounded by the endplate and the sidewalls; and
first and second radio frequency (RF) coupling receptacles coupled to at least one of the sidewalls or the endplate, wherein the first and second RF coupling receptacles are configured to pass a RF signal through the cavity,
wherein the endplate comprises a suppression unit operable to suppress undesired resonant modes.

19. The measurement system of claim 18, wherein the suppression unit comprises a plurality of coplanar conducting loops disposed on an interior-facing surface of the endplate, wherein each loop of the plurality of conducting loops is electrically isolated from other loops of the plurality of conducting loops.

20. The measurement system of claim 19, wherein the endplate comprises a first endplate, wherein the measurement system further comprises a second endplate disposed opposite the first endplate such that the cavity is bounded by the sidewalls, the first endplate and the second endplate, wherein the second endplate comprises first and second regions, wherein the first region comprises a material that is substantially non-lossy at frequencies of interest, and wherein the second region comprises a lossy material.

21. The measurement system of claim 18, wherein the suppression unit comprises first and second regions, wherein the first region comprises a material that is substantially non-lossy at frequencies of interest, and wherein the second region comprises a lossy material.

22. The measurement system of claim 21, wherein the endplate comprises an interior-facing surface and an exterior-facing surface disposed opposite the interior-facing surface, wherein the second region comprises a toroidal shape having a cross-section, wherein the interior-facing surface of the endplate consists of a first surface of the first region, and wherein the exterior-facing surface of the endplate comprises a second surface of the first region and a surface of the second region, wherein the cross-section of the toroidal shape comprises a generally triangular shape so as to define a greater cross-section further from the cavity.

23. The measurement system of claim 21, wherein the material that is substantially non-lossy at frequencies of interest comprises a metal.

24. The measurement system of claim 18, further comprising a movement mechanism to mechanically move the endplate relative to the sidewalls.

* * * * *